United States Patent
Juergen et al.

(10) Patent No.: US 11,133,529 B2
(45) Date of Patent: Sep. 28, 2021

(54) FLUORINATED ACRYLATES AS ADDITIVES FOR LI-ION BATTERY ELECTROLYTES

(71) Applicant: Gotion Inc., Fremont, CA (US)

(72) Inventors: Frank Juergen, Ludwigshafen (DE); Stefano Meini, Munich (DE); Michael Schmidt, Alsbach-Haehnlein (DE); Martin Merger, Frankenthal (DE)

(73) Assignee: Gotion, Inc., Fremont, CA (US)

( * ) Notice: Subject to any disclaimer, the term of this patent is extended or adjusted under 35 U.S.C. 154(b) by 345 days.

(21) Appl. No.: 15/762,349

(22) PCT Filed: Sep. 13, 2016

(86) PCT No.: PCT/EP2016/071515
§ 371 (c)(1),
(2) Date: Mar. 22, 2018

(87) PCT Pub. No.: WO2017/050609
PCT Pub. Date: Mar. 30, 2017

(65) Prior Publication Data
US 2018/0277898 A1    Sep. 27, 2018

(30) Foreign Application Priority Data

Sep. 23, 2015 (EP) .................... 15186503

(51) Int. Cl.
| | |
|---|---|
| *H01M 10/0567* | (2010.01) |
| *C07D 307/33* | (2006.01) |
| *H01M 10/052* | (2010.01) |
| *C07C 69/65* | (2006.01) |
| *C07C 69/533* | (2006.01) |
| *H01M 10/0525* | (2010.01) |
| *H01M 10/0569* | (2010.01) |

(52) U.S. Cl.
CPC ....... *H01M 10/0567* (2013.01); *C07C 69/533* (2013.01); *C07C 69/65* (2013.01); *C07D 307/33* (2013.01); *H01M 10/052* (2013.01); *H01M 10/0525* (2013.01); *H01M 10/0569* (2013.01); *H01M 2300/0025* (2013.01); *H01M 2300/0037* (2013.01)

(58) Field of Classification Search
CPC ......... H01M 10/0567; H01M 10/0569; H01M 10/0525; H01M 10/052; H01M 2300/0037; H01M 2300/0025; C07D 307/33; C07C 69/65; C07C 69/533
See application file for complete search history.

(56) References Cited

U.S. PATENT DOCUMENTS

| | | | | |
|---|---|---|---|---|
| 2003/0232276 A1 * | 12/2003 | Poss | ....................... | C07C 69/65 |
| | | | | 526/292.1 |
| 2009/0197167 A1 * | 8/2009 | Olschimke | ........ | H01M 10/0567 |
| | | | | 429/188 |
| 2013/0164605 A1 | 6/2013 | Shimura et al. | | |
| 2015/0118548 A1 * | 4/2015 | Suguro | ............. | H01M 10/0567 |
| | | | | 429/188 |

FOREIGN PATENT DOCUMENTS

| | | | |
|---|---|---|---|
| JP | 2003-100342 A | | 4/2003 |
| JP | 2005-518476 A | | 6/2005 |
| JP | 2005340151 A | | 12/2005 |
| JP | 2009-001518 A | | 1/2009 |
| JP | 2009-152133 | * | 7/2009 |
| JP | 2009152133 A | | 7/2009 |
| JP | 2011-162509 A | | 8/2011 |
| JP | 2012-043632 A | | 3/2012 |
| JP | 2012-89457 | * | 5/2012 |
| WO | 2013/008439 A1 | | 1/2013 |
| WO | WO 2013/183490 | * | 12/2013 |

OTHER PUBLICATIONS

Chinese Office Action issued in corresponding Chinese Patent Application No. 201680055729.6 dated Jul. 26, 2019.
Japanese Office Action dated Jun. 2, 2020 in Japanese Patent Application No. 2018-515285, together with an English language translation.

\* cited by examiner

*Primary Examiner* — Laura Weiner
(74) *Attorney, Agent, or Firm* — Scully, Scott, Murphy & Presser, P.C.

(57) ABSTRACT

A compound of formula (I)

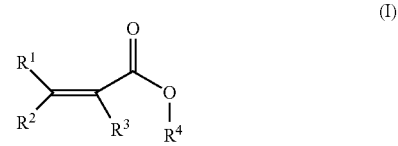

for use in electrolyte compositions for electrochemical cells, wherein $R^1$ and $R^2$ are selected independently from each other from H, F, CN, R', OR', OC(O)R', and OP(O)R''$_2$, $R^3$ is selected from H, $C_1$ to $C_{12}$ alkyl, $C_3$ to $C_6$ (hetero)cycloalkyl, $C_2$ to $C_{12}$ alkenyl, $C_2$ to $C_{12}$ alkynyl, $C_5$ to $C_{12}$ (hetero)aryl, and $C_6$ to $C_{24}$ (hetero)aralkyl, $R^4$ is selected from $C_1$ to $C_{12}$ alkyl, $C_3$ to $C_6$ (hetero)cycloalkyl, $C_2$ to $C_{12}$ alkenyl, $C_2$ to $C_{12}$ alkynyl, $C_5$ to $C_{12}$ (hetero)aryl, and $C_6$ to $C_{24}$ (hetero)aralkyl, or $R^3$ and $R^4$ are bound together and form together with the group —C—C(O)—O— a 5- to 6-membered heterocycle which may be substituted by one or more substituents selected from F and optionally fluorinated $C_1$ to $C_{12}$ alkyl.

10 Claims, No Drawings

FLUORINATED ACRYLATES AS ADDITIVES FOR LI-ION BATTERY ELECTROLYTES

CROSS-REFERENCE TO RELATED APPLICATION(S)

This application is a 371 application of International Application PCT/EP2016/071515, filed on Sep. 13, 2016, which claims priority to European Patent Application No. 15186503.7, filed on Sep. 23, 2015, the content of which is hereby incorporated by reference in its entirety.

DETAILED DESCRIPTION

The present disclosure relates to compounds of formula (I)

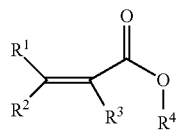

wherein $R^1$, $R^2$, $R^3$, and $R^4$ are defined below, to the use of compounds of formula (I) in electrolyte compositions, and to electrochemical cells comprising such electrolyte composition.

Storing electrical energy is a subject of still growing interest. Efficient storage of electric energy allows electric energy to be generated when it is advantageous and used when needed. Secondary electrochemical cells are well suited for this purpose due to their reversible conversion of chemical energy into electrical energy and vice versa (rechargeability). Secondary lithium batteries are of special interest for energy storage since they provide high energy density and specific energy due to the small atomic weight of the lithium ion, and the high cell voltages that can be obtained (typically 2 to 5 V) in comparison with other battery systems. For that reason, these systems have become widely used as a power source for many portable electronics such as cellular phones, laptop computers, mini-cameras, etc.

Secondary lithium batteries like lithium ion batteries typically comprise electrolyte compositions containing one or more organic aprotic solvents, e.g. non-aqueous solvents like organic carbonates, ethers, esters, and ionic liquids, at least one conducting salt like $LiPF_6$ and optionally one or more additives for enhancing the performance of electrolyte composition and battery. Useful additives are for example SEI additives, flame retardant additives, water scavenger, overcharge protection additives. A lot of research is ongoing in respect to additives for use in electrolyte compositions to further improve the performance of the electrochemical cell containing the electrolyte composition in many different aspects, e.g. cycle life time, high temperature characteristics, safety, etc.

During charge and discharge of lithium ion batteries various reactions take place at different cell potentials. It is known that during the first charging process (also referred to as "formation") of a lithium ion battery usually an electrically insulating film is formed on the negative electrode surface. This film is often called solid electrolyte interface (SEI) and it is formed by reductive decomposition of components of the electrolyte formulation like solvents, e.g. carbonates, esters, and ethers, and conductive salts on the surface of the anode, especially if the anode active material is a carbonaceous material like graphite. The SEI is permeable for lithium ions and prevents further reduction of the electrolyte by avoiding direct contact with the anode and vice versa. A certain amount of the available lithium from the cathode material is irreversibly consumed for the formation of the SEI, and it is not any more available for cycling. Structure and properties of the SEI may be significantly influenced by addition of suitable chemical compounds which are easily reduced on the anode surface, leading to the formation of a film with different properties than that produced by the base formulation. The use of those suitable compounds represents also a possibility to reduce the amount of irreversibly consumed lithium and thus to improve cell's capacity. The SEI has a significant influence on cycling stability, calendar ageing, and durability (high-current resistance) of an electrochemical or electrooptical device. Different SEI forming additives are known, e.g. vinylene carbonate.

Despite the additives already known for improving the performance of electrochemical cells there is still the demand for further additives for improving properties and performance of electrochemical cells like long cycle life time, cycle stability, rate capability and storage stability of electrochemical cells, e.g. resulting in good capacity retention after storage. It is the object of the present disclosure to provide further additives for electrochemical cells which improve the properties and the performance of electrochemical cell and to provide electrolyte compositions and electrochemical cells showing good properties and performance like long cycle life time, high cycle stability, good rate capability and good capacity retention after high temperature storage.

This object is achieved by compounds of formula (I)

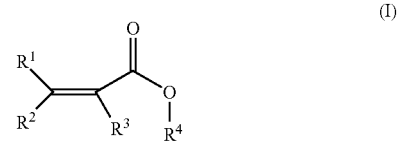

wherein
$R^1$ and $R^2$ are selected independently from each other from H, F, CN, R', OR', OC(O)R', and OP(O)R''$_2$,
  wherein R' is selected independently from $C_1$ to $C_{12}$ alkyl, $C_3$ to $C_6$ (hetero)cycloalkyl, $C_2$ to $C_{12}$ alkenyl, $C_2$ to $C_{12}$ alkynyl, $C_5$ to $C_{12}$ (hetero)aryl, and $C_6$ to $C_{24}$ (hetero)aralkyl, wherein alkyl, (hetero)cycloalkyl, alkenyl, alkynyl, (hetero)aryl, and (hetero)aralkyl may be substituted by one or more substituents selected from F and CN,
  wherein R'' is selected independently from OR' and R' and wherein the two R'' may form together with the P-atom a 5- to 6-membered heterocycle, and
  wherein at least one of $R^1$ and $R^2$ comprises one or more F;
$R^3$ is selected from H, $C_1$ to $C_{12}$ alkyl, $C_3$ to $C_6$ (hetero)cycloalkyl, $C_2$ to $C_{12}$ alkenyl, $C_2$ to $C_{12}$ alkynyl, $C_5$ to $C_{12}$ (hetero)aryl, and $C_6$ to $C_{24}$ (hetero)aralkyl, wherein alkyl, (hetero)cycloalkyl, alkenyl, alkynyl, (hetero)aryl, and (hetero)aralkyl may be substituted by one or more substituents selected from F and CN;
$R^4$ is selected from $C_1$ to $C_{12}$ alkyl, $C_3$ to $C_6$ (hetero)cycloalkyl, $C_2$ to $C_{12}$ alkenyl, $C_2$ to $C_{12}$ alkynyl, $C_5$ to $C_{12}$ (hetero)aryl, and $C_6$ to $C_{24}$ (hetero)aralkyl, wherein alkyl, (hetero)cycloalkyl, alkenyl, alkynyl, (hetero)aryl, and (hetero)aralkyl may be substituted by one or more substituents selected from F and CN;

or $R^3$ and $R^4$ are bound together and form together with the group —C—C(O)—O— a 5- to 6-membered heterocycle which may be substituted by one or more substituents selected from F and optionally fluorinated $C_1$ to $C_{12}$ alkyl; and the use of compounds of formula (I) as additives in electrochemical cell, e.g. in electrolyte compositions for electrochemical cells, in particular as SEI forming additive. The object is also achieved by an electrolyte composition containing at least one compound of formula (I) and by electrochemical cells comprising the electrolyte composition.

Compounds of formula (I) are suited as SEI additives in lithium ion batteries and allow for example the use of propylene carbonate containing electrolytes in secondary cells comprising a graphite based anode. Electrochemical cells comprising an electrolyte compositions containing a compound of general formula (I) show good capacity retention.

In the following the disclosure is described in detail.

One aspect of the disclosure relates to electrolyte compositions containing at least one compound of formula (I)

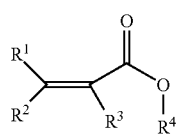

(I)

wherein $R^1$ and $R^2$ are selected independently from each other from H, F, CN, R', OR', OC(O)R', and OP(O)R''$_2$, wherein at least one of $R^1$ and $R^2$ comprises one or more F. Preferably both $R^1$ and $R^2$ are not H, i.e. $R^1$ and $R^2$ are selected independently from each other from F, CN, R', OR', OC(O)R', and OP(O)R''$_2$.

R' is selected independently from $C_1$ to $C_{12}$ alkyl, $C_3$ to $C_6$ (hetero)cycloalkyl, $C_2$ to $C_{12}$ alkenyl, $C_2$ to $C_{12}$ alkynyl, $C_5$ to $C_{12}$ (hetero)aryl, and $C_6$ to $C_{24}$ (hetero)aralkyl, wherein alkyl, (hetero)cycloalkyl, alkenyl, alkynyl, (hetero)aryl, and (hetero)aralkyl may be substituted by one or more substituents selected from F and CN; preferably R' is selected independently from $C_1$ to $C_{12}$ alkyl, $C_2$ to $C_{12}$ alkenyl, $C_2$ to $C_{12}$ alkynyl, and $C_5$ to $C_{12}$ (hetero)aryl, wherein alkyl, alkenyl, alkynyl, and (hetero)aryl may be substituted by one or more substituents selected from F and CN.

R" is selected independently from OR' and R' and the two R" may form together with the P-atom a 5- to 6-membered heterocycle. Preferably R" is selected independently from $OC_1$ to $C_{12}$ alkyl, $OC_2$ to $C_{12}$ alkenyl, $OC_2$ to $C_{12}$ alkynyl, $C_5$ to $C_{12}$ (hetero)aryl, $C_1$ to $C_{12}$ alkyl, $C_2$ to $C_{12}$ alkenyl, $C_2$ to $C_{12}$ alkynyl, and $C_5$ to $C_{12}$ (hetero)aryl, wherein alkyl, alkenyl, alkynyl, and (hetero)aryl may be substituted by one or more substituents selected from F and CN.

$R^3$ is selected from H, $C_1$ to $C_{12}$ alkyl, $C_3$ to $C_6$ (hetero)cycloalkyl, $C_2$ to $C_{12}$ alkenyl, $C_2$ to $C_{12}$ alkynyl, $C_5$ to $C_{12}$ (hetero)aryl, and $C_6$ to $C_{24}$ (hetero)aralkyl, wherein alkyl, (hetero)cycloalkyl, alkenyl, alkynyl, (hetero)aryl, and (hetero)aralkyl may be substituted by one or more substituents selected from F and CN; preferably $R^3$ is selected from H and $C_1$ to $C_{12}$ alkyl, which may be substituted by one or more substituents selected from F and CN, more preferred preferably $R^3$ is selected from H and $C_1$ to $C_{12}$ alkyl.

$R^4$ is selected from $C_1$ to $C_{12}$ alkyl, $C_3$ to $C_6$ (hetero)cycloalkyl, $C_2$ to $C_{12}$ alkenyl, $C_2$ to $C_{12}$ alkynyl, $C_5$ to $C_{12}$ (hetero)aryl, and $C_6$ to $C_{24}$ (hetero)aralkyl, wherein alkyl, (hetero)cycloalkyl, alkenyl, alkynyl, (hetero)aryl, and (hetero)aralkyl may be substituted by one or more substituents selected from F and CN, preferably $R^4$ is selected from $C_1$ to $C_{12}$ alkyl, $C_2$ to $C_{12}$ alkenyl, $C_2$ to $C_{12}$ alkynyl, and $C_5$ to $C_{12}$ (hetero)aryl, wherein alkyl, alkenyl, alkynyl, and (hetero)aryl may be substituted by one or more substituents selected from F and CN, and most preferred $R^4$ is selected from H and $C_1$ to $C_{12}$ alkyl which may be substituted by one or more substituents selected from F and CN.

It is also possible that $R^3$ and $R^4$ are bound together and form together with the group —C—C(O)—O— a 5- to 6-membered heterocycle, preferably they form a 5-membered heterocycle. The heterocycle may be substituted by one or more substituents selected from F and optionally fluorinated $C_1$ to $C_{12}$ alkyl, preferably the heterocycle may be substituted by one or more substituents selected from F and optionally fluorinated $C_1$ to $C_6$ alkyl.

The term "$C_1$ to $C_{12}$ alkyl" as used herein means a straight or branched saturated hydrocarbon group with 1 to 12 carbon atoms having one free valence and includes, e.g., methyl, ethyl, n-propyl, isopropyl, n-butyl, isobutyl, tert-butyl, n-pentyl, iso-pentyl, 2,2-dimethylpropyl, n-hexyl, iso-hexyl, 2-ethyl hexyl, n-heptyl, iso-heptyl, n-octyl, iso-octyl, n-nonyl, n-decyl and the like. Preferred are $C_1$-$C_{10}$ alkyl groups, more preferred are $C_1$-$C_6$ alkyl groups, even more preferred are $C_1$-$C_4$ alkyl groups, and most preferred are methyl, ethyl, and n- and iso-propyl.

The term "$C_3$ to $C_6$ (hetero)cycloalkyl" as used herein means a saturated 3- to 6-membered hydrocarbon cycle having one free valence wherein one or more of the C— atoms of the saturated cycle may be replaced independently from each other by a heteroatom selected from N, S, O and P. Examples of $C_3$ to $C_6$ (hetero)cycloalkyl are cyclopropyl, oxiranyl, cyclopentyl, pyrrolidinyl, tetrahydrofuryl, cyclohexyl, piperidyl and morpholinyl.

The term "$C_2$ to $C_{12}$ alkenyl" as used herein refers to an unsaturated straight or branched hydrocarbon group with 2 to 12 carbon atoms having one free valence. Unsaturated means that the alkenyl group contains at least one C—C double bond. $C_2$-$C_{12}$ alkenyl includes for example ethenyl, 1-propenyl, 2-propenyl, 1-n-butenyl, 2-n-butenyl, iso-butenyl, 1-pentenyl, 1-hexenyl, 1-heptenyl, 1-octenyl, 1-nonenyl, 1-decenyl and the like. Preferred are $C_2$-$C_{10}$ alkenyl groups, more preferred are $C_2$-$C_6$ alkenyl groups, even more preferred are $C_2$-$C_4$ alkenyl groups and in particular ethenyl and 1-propen-3-yl (allyl).

The term "$C_2$ to $C_{12}$ alkynyl" as used herein refers to an unsaturated straight or branched hydrocarbon group with 2 to 12 carbon atoms having one free valence, wherein the hydrocarbon group contains at least one C—C triple bond. $C_2$-$C_{12}$ alkynyl includes for example ethynyl, 1-propynyl, 2-propynyl, 1-n-butinyl, 2-n-butynyl, iso-butinyl, 1-pentynyl, 1-hexynyl, -heptynyl, 1-octynyl, 1-nonynyl, 1-decynyl and the like and the like. Preferred are $C_2$-$C_{10}$ alkynyl, more preferred are $C_2$-$C_6$ alkynyl, even more preferred are $C_2$-$C_4$ alkynyl, in particular preferred are ethynyl and 1-propyn-3-yl (propargyl).

The term "$C_5$ to $C_{12}$ (hetero)aryl" as used herein denotes an aromatic 5- to 12-membered hydrocarbon cycle or condensed cycles having one free valence wherein one or more of the C— atoms of the aromatic cycle(s) may be replaced independently from each other by a heteroatom selected from N, S, O, and P. Examples of $C_5$-$C_{12}$ (hetero)aryl are furanyl, pyridinyl, phenyl and naphtyl. Preferred is phenyl.

The term "$C_6$ to $C_{24}$ (hetero)aralkyl" as used herein denotes an aromatic 5- to 12-membered aromatic hydrocarbon cycle or condensed aromatic cycles substituted by one or more $C_1$-$C_6$ alkyl, wherein the wherein one or more of the C— atoms of the aromatic cycle(s) may be replaced independently from each other by a heteroatom selected from N, S, O, and P. The $C_6$-$C_{24}$ (hetero)aralkyl group contains in total 6 to 24 C-atoms and has one free valence. The free valence may be located at the (hetero)aromatic cycle or at a $C_1$-$C_6$ alkyl group, i.e. $C_6$-$C_{24}$ (hetero)aralkyl group may be bound via the aromatic part or via the alkyl part of the (hetero)aralkyl group. Examples of $C_6$-$C_{24}$ (hetero)aralkyl are methylphenyl, 2-methylfuranyl, 3-ethylpyridinyl 1,2-dimethylphenyl, 1,3-dimethylphenyl, 1,4-dimethylphenyl, ethylphenyl, 2-propylphenyl, and the like.

Preferably at least one of $R^1$ and $R^2$ is selected from F and optionally fluorinated $C_1$ to $C_{12}$ alkyl, and more preferred both $R^1$ and $R^2$ are selected from F and optionally fluorinated $C_1$ to $C_{12}$ alkyl. Optionally fluorinated $C_1$ to $C_{12}$ alkyl include for example methyl, monofluoromethyl, difluoromethyl, trifluoromethyl, ethyl, monoflruoroethyl, 1,1,1-trifluoroethyl, i-propyl, n-propyl, 1,1,1,3,3,3-hexafluoropropyl, and the like In case at least one of $R^1$ and $R^2$ is selected from fluorinated $C_1$ to $C_{12}$ alkyl, it is preferred to select the at least one of $R^1$ and $R^2$ from perfluorinated $C_1$ to $C_{12}$ alkyl, more preferred the at least one of $R^1$ and $R^2$ is selected from $CF_3$, $C_2F_5$, n-$C_3F_7$, and i-$C_3F_7$, and even more preferred at least one of $R^1$ and $R^2$ is $CF_3$.

According to another embodiment both $R^1$ and $R^2$ are selected from fluorinated $C_1$ to $C_{12}$ alkyl, more preferred both $R^1$ and $R^2$ are selected from perfluorinated $C_1$ to $C_{12}$ alkyl, even more preferred both $R^1$ and $R^2$ are selected from $CF_3$, $C_2F_5$, n-$C_3F_7$, and i-$C_3F_7$, and even more preferred at least one of $R^1$ and $R^2$ is $CF_3$.

The term "fluorinated alkyl" means, that one or more H of the alkyl group is substituted by F.

The term "perfluorinated alkyl" means, that all H present in the alkyl group are substituted by F.

Examples of compounds of formula (I) are compounds of formulae (I.1) to (I.4)

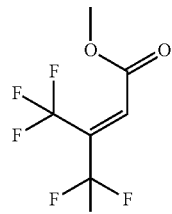
(I.1)

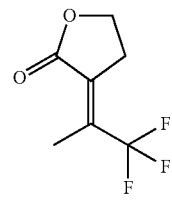
(I.2)

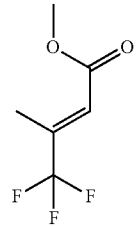
(I.3)

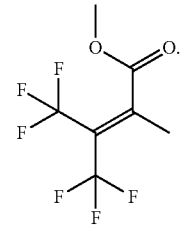
(I.4)

The preparation of compounds of formula (I) is known to person skilled in the art, compounds of formula (I) may be prepared in analogy to Y. M. Saunier, R. Danion-Bougot, D. Danion & R. Carrie, Tetrahedron 32, 1995 (1976); J. Chem. Ecolog. 5, 773 (1979).

According to one aspect of the disclosure the compounds of the formula (I), as described above or as described as being preferred, are used in electrolyte compositions for electrochemical cells, preferably the compounds of formula (I) are used as additives in electrolyte compositions for electrochemical cells, in particular preferred they are used as SEI forming additives in electrolyte compositions for electrochemical cells.

SEI forming additives are known to the person skilled in the art. An SEI forming additive according to the present disclosure is a compound which decomposes on an electrode to form a passivation layer on the electrode which prevents degradation of the electrolyte and/or the electrode. In this way, the lifetime of a battery is significantly extended. Preferably the SEI forming additive forms a passivation layer on the anode. An anode in the context of the present disclosure is understood as the negative electrode of a battery. Preferably, the anode has a reduction potential of 1 Volt or less vs. Li$^+$/Li redox couple, such as a graphite anode. In order to determine if a compound qualifies as anode film forming additive, an electrochemical cell can be prepared comprising a graphite electrode and a lithium-ion containing cathode, for example lithium cobalt oxide, and an electrolyte containing a small amount of said compound, typically from 0.01 to 10 wt.-% of the electrolyte composition, preferably from 0.05 to 5 wt.-% of the electrolyte composition.

Upon application of a small current between anode and cathode, the anode potential can be swept from open circuit potential (OCP) to the proximity of Li$^+$/Li redox potential (e.g., 0.005V$_{Li}$). Reduction processes of the electrolyte solution components will be visible as peaks in the cell's differential capacity plot (derivative of capacity by potential, vs. potential). The onset potential, peak intensity and area of those peaks can be taken into consideration to determine whether an additive can be regarded as SEI forming additive. When comparing the differential capacity plots of a base electrolyte formulation and of the base formulation+additive, an ideal SEI forming additive will have reduction peak (typically at higher voltages) of similar intensity and area of those appearing for the base electrolyte formulation in the first cycle; furthermore, the peak(s) intensity(ies) of the base electrolyte formulation shall be highly reduced or substantially modified in nature. If those requirements are fulfilled, the compound can be regarded as SEI forming additive. Some less efficient SEI forming additives may have much higher peak intensity and peak area, however the reduction/modification of the standard solution's peak intensity should always be present.

Accordingly, the total concentration of the at least one compound of formula (I) present in the electrolyte composition is typically 0.01 to 10 wt.-% preferred 0.05 to 5 wt.-%, more preferred 0.125 to 2.5 wt.-%, and most preferred 0.25 to 1.5 wt.-%, based on the total weight of the electrolyte composition. Usually the compound(s) of formula (I) are added to the electrolyte composition in the desired amount during or after manufacture of the electrolyte composition.

Preferably the electrolyte composition additionally at least one aprotic organic solvent, at least one conducting salt and optionally at least one further additive different from the compounds of formula (I).

Viewed chemically, an electrolyte composition is any composition which comprises free ions and as a result is electrically conductive. The most typical electrolyte composition is an ionic solution, although molten electrolyte compositions and solid electrolyte compositions are likewise possible. An electrolyte composition of the disclosure is therefore an ionic conductive medium, primarily due to the presence of at least one substance which is present in a dissolved and/or molten state.

The electrolyte composition preferably contains at least one aprotic organic solvent, more preferred at least two aprotic organic solvents. According to one embodiment the electrolyte composition may contain up to ten aprotic organic solvents.

The at least one aprotic organic solvent is preferably selected from cyclic and acyclic organic carbonates, di-$C_1$-$C_{10}$-alkylethers, di-$C_1$-$C_4$-alkyl-$C_2$-$C_6$-alkylene ethers and polyethers, cyclic ethers, cyclic and acyclic acetales and ketales, orthocarboxylic acids esters, cyclic and acyclic esters of carboxylic acids, cyclic and acyclic sulfones, and cyclic and acyclic nitriles and dinitriles.

More preferred the at least one aprotic organic solvent is selected from cyclic and acyclic carbonates, di-$C_1$-$C_{10}$-alkylethers, di-$C_1$-$C_4$-alkyl-$C_2$-$C_6$-alkylene ethers and polyethers, cyclic and acyclic acetales and ketales, and cyclic and acyclic esters of carboxylic acids, even more preferred the electrolyte composition contains at least one aprotic organic solvent selected from cyclic and acyclic carbonates, and most preferred the electrolyte composition contains at least two aprotic organic solvents selected from cyclic and acyclic carbonates, in particular preferred the electrolyte composition contains at least one aprotic solvent selected from cyclic carbonates and at least one aprotic organic solvent selected from acyclic carbonates.

The aprotic organic solvents may be partly halogenated, e.g. they may be partly fluorinated, partly chlorinated or partly brominated, and preferably they may be partly fluorinated. "Partly halogenated" means, that one or more H of the respective molecule is substituted by a halogen atom, e.g. by F, Cl or Br. Preference is given to the substitution by F. The at least one solvent may be selected from partly halogenated and non-halogenated aprotic organic solvents i.e. the electrolyte composition may contain a mixture of partly halogenated and non-halogenated aprotic organic solvents.

Examples of cyclic carbonates are ethylene carbonate (EC), propylene carbonate (PC) and butylene carbonate (BC), wherein one or more H of the alkylene chain may be substituted by F and/or an $C_1$ to $C_4$ alkyl group, e.g. 4-methyl ethylene carbonate, monofluoroethylene carbonate (FEC), and cis- and trans-difluoroethylene carbonate. Preferred cyclic carbonates are ethylene carbonate, monofluoroethylene carbonate and propylene carbonate, in particular ethylene carbonate.

Examples of acyclic carbonates are di-$C_1$-$C_{10}$-alkylcarbonates, wherein each alkyl group is selected independently from each other, preferred are di-$C_1$-$C_4$-alkylcarbonates. Examples are e.g. diethyl carbonate (DEC), ethyl methyl carbonate (EMC), dimethyl carbonate (DMC), and methylpropyl carbonate. Preferred acyclic carbonates are diethyl carbonate (DEC), ethyl methyl carbonate (EMC), dimethyl carbonate (DMC).

In one embodiment of the disclosure the electrolyte composition contains mixtures of acyclic organic carbonates and cyclic organic carbonates at a ratio by weight of from 1:10 to 10:1, preferred of from 3:1 to 1:1.

According to the disclosure each alkyl group of the di-$C_1$-$C_{10}$-alkylethers is selected independently from the other. Examples of di-$C_1$-$C_{10}$-alkylethers are dimethylether, ethylmethylether, diethylether, methylpropylether, diisopropylether, and di-n-butylether.

Examples of di-$C_1$-$C_4$-alkyl-$C_2$-$C_6$-alkylene ethers are 1,2-dimethoxyethane, 1,2-diethoxyethane, diglyme (diethylene glycol dimethyl ether), triglyme (triethyleneglycol dimethyl ether), tetraglyme (tetraethyleneglycol dimethyl ether), and diethylenglycoldiethylether.

Examples of suitable polyethers are polyalkylene glycols, preferably poly-$C_1$-$C_4$-alkylene glycols and especially polyethylene glycols. Polyethylene glycols may comprise up to 20 mol % of one or more $C_1$-$C_4$-alkylene glycols in copolymerized form. Polyalkylene glycols are preferably dimethyl- or diethyl-end-capped polyalkylene glycols. The molecular weight $M_w$ of suitable polyalkylene glycols and especially of suitable polyethylene glycols may be at least 400 g/mol. The molecular weight $M_w$ of suitable polyalkylene glycols and especially of suitable polyethylene glycols may be up to 5 000 000 g/mol, preferably up to 2 000 000 g/mol.

Examples of cyclic ethers are 1,4-dioxane, tetrahydrofuran, and their derivatives like 2-methyl tetrahydrofuran.

Examples of acyclic acetals are 1,1-dimethoxymethane and 1,1-diethoxymethane. Examples of cyclic acetals are 1,3-dioxane, 1,3-dioxolane, and their derivatives such as methyl dioxolane.

Examples of acyclic orthocarboxylic acid esters are tri-$C_1$-$C_4$ alkoxy methane, in particular trimethoxymethane and triethoxymethane. Examples of suitable cyclic orthocarboxylic acid esters are 1,4-dimethyl-3,5,8-trioxabicyclo[2.2.2]octane and 4-ethyl-1-methyl-3,5,8-trioxabicyclo[2.2.2]octane.

Examples of acyclic esters of carboxylic acids are ethyl and methyl formate, ethyl and methyl acetate, ethyl and methyl proprionate, and ethyl and methyl butanoate, and esters of dicarboxylic acids like 1,3-dimethyl propanedioate. An example of a cyclic ester of carboxylic acids (lactones) is γ-butyrolactone.

Examples of cyclic and acyclic sulfones are ethyl methyl sulfone, dimethyl sulfone, and tetrahydrothiophene-S,S-dioxide (sulfolane).

Examples of cyclic and acyclic nitriles and dinitriles are adipodinitrile, acetonitrile, propionitrile, and butyronitrile.

The inventive electrolyte composition usually contains at least one conducting salt. The electrolyte composition functions as a medium that transfers ions participating in the electrochemical reaction taking place in an electrochemical cell. The conducting salt(s) present in the electrolyte are usually solvated in the aprotic organic solvent(s). Preferably the conducting salt is a lithium salt. The conducting salt is preferably selected from the group consisting of Li[F$_{6-x}$P(C$_y$F$_{2y+1}$)$_x$], wherein x is an integer in the range from 0 to 6 and y is an integer in the range from 1 to 20;

Li[B(R$^1$)$_4$], Li[B(R$^I$)$_2$(OR$^{II}$O)] and Li[B(OR$^{II}$O)$_2$] wherein each R$^I$ is independently from each other selected from F, Cl, Br, I, C$_1$-C$_4$ alkyl, C$_2$-C$_4$ alkenyl, C$_2$-C$_4$ alkynyl, OC$_1$-C$_4$ alkyl, OC$_2$-C$_4$ alkenyl, and OC$_2$-C$_4$ alkynyl wherein alkyl, alkenyl, and alkynyl may be substituted by one or more OR$^{III}$, wherein R$^{III}$ is selected from C$_1$-C$_6$ alkyl, C$_2$-C$_6$ alkenyl, and C$_2$-C$_6$ alkynyl, and (OR$^{II}$O) is a bivalent group derived from a 1,2- or 1,3-diol, a 1,2- or 1,3-dicarboxlic acid or a 1,2- or 1,3-hydroxycarboxylic acid, wherein the bivalent group forms a 5- or 6-membered cycle via the both oxygen atoms with the central B-atom;

LiClO$_4$; LiAsF$_6$; LiCF$_3$SO$_3$; Li$_2$SiF$_6$; LiSbF$_6$; LiAlCl$_4$, Li(N(SO$_2$F)$_2$), lithium tetrafluoro (oxalato) phosphate; lithium oxalate; and salts of the general formula Li[Z(C$_n$F$_{2n+1}$SO$_2$)$_m$], where m and n are defined as follows:

m=1 when Z is selected from oxygen and sulfur,
m=2 when Z is selected from nitrogen and phosphorus,
m=3 when Z is selected from carbon and silicon, and
n is an integer in the range from 1 to 20.

Suited 1,2- and 1,3-diols from which the bivalent group (OR$^{II}$O) is derived may be aliphatic or aromatic and may be selected, e.g., from 1,2-dihydroxybenzene, propane-1,2-diol, butane-1,2-diol, propane-1,3-diol, butan-1,3-diol, cyclohexyl-trans-1,2-diol and naphthalene-2,3-diol which are optionally are substituted by one or more F and/or by at least one straight or branched non-fluorinated, partly fluorinated, or fully fluorinated C$_1$-C$_4$ alkyl group. An example for such 1,2- or 1,3-diole is 1,1,2,2-tetra(trifluoromethyl)-1,2-ethane diol.

"Fully fluorinated C$_1$-C$_4$ alkyl group" means, that all H-atoms of the alkyl group are substituted by F.

Suited 1,2- or 1,3-dicarboxlic acids from which the bivalent group (OR$^{II}$O) is derived may be aliphatic or aromatic, for example oxalic acid, malonic acid (propane-1,3-dicarboxylic acid), phthalic acid or isophthalic acid, preferred is oxalic acid. The 1,2- or 1,3-dicarboxlic acid are optionally substituted by one or more F and/or by at least one straight or branched non-fluorinated, partly fluorinated, or fully fluorinated C$_1$-C$_4$ alkyl group.

Suited 1,2- or 1,3-hydroxycarboxylic acids from which the bivalent group (OR$^{II}$O) is derived may be aliphatic or aromatic, for example salicylic acid, tetrahydro salicylic acid, malic acid, and 2-hydroxy acetic acid, which are optionally substituted by one or more F and/or by at least one straight or branched non-fluorinated, partly fluorinated, or fully fluorinated C$_1$-C$_4$ alkyl group. An example for such 1,2- or 1,3-hydroxycarboxylic acids is 2,2-bis(trifluoromethyl)-2-hydroxy-acetic acid.

Examples of Li[B(R$^I$)$_4$], Li[B(R$_I$)$_2$(OR$^{II}$O)] and Li[B(OR$^{II}$O)$_2$] are LiBF$_4$, lithium difluoro oxalato borate and lithium dioxalato borate.

Preferably the at least one conducting salt is selected from LiPF$_6$, LiBF$_4$, and LiPF$_3$(CF$_2$CF$_3$)$_3$, more preferred the conducting salt is selected from LiPF$_6$ and LiBF$_4$, and the most preferred conducting salt is LiPF$_6$.

The at least one conducting salt is usually present at a minimum concentration of at least 0.1 m/1, preferably the concentration of the at least one conducting salt is 0.5 to 2 mol/l based on the entire electrolyte composition.

The electrolyte composition according to the present disclosure may contain at least one further additive different from the compounds of formula (I). The further additive may be selected from polymers, SEI forming additives, flame retardants, overcharge protection additives, wetting agents, HF and/or H$_2$O scavenger, stabilizer for LiPF$_6$ salt, ionic salvation enhancer, corrosion inhibitors, gelling agents, and the like.

Examples for polymers used in electrolyte compositions are polyvinylidene fluoride, polyvinylidene-hexafluoropropylene copolymers, polyvinylidene-hexafluoropropylene-chlorotrifluoroethylene copolymers, Nafion, polyethylene oxide, polymethyl methacrylate, polyacrylonitrile, polypropylene, polystyrene, polybutadiene, polyethylene glycol, polyvinylpyrrolidone, polyaniline, polypyrrole and/or polythiophene. These polymers may be added to electrolyte compositions containing a solvent or solvent mixture in order to convert liquid electrolytes into quasi-solid or solid electrolytes and thus to improve solvent retention, especially during ageing.

Examples of flame retardants are organic phosphorous compounds like cyclophosphazenes, phosphoramides, alkyl and/or aryl tri-substituted phosphates, alkyl and/or aryl di- or tri-substituted phosphites, alkyl and/or aryl di-substituted phosphonates, alkyl and/or aryl tri-substituted phosphines, and fluorinated derivatives thereof.

Examples of HF and/or H$_2$O scavenger are optionally halogenated cyclic and acyclic silylamines.

Examples of overcharge protection additives are cyclohexylbenzene, o-terphenyl, p-terphenyl, and biphenyl and the like, preferred are cyclohexylbenzene and biphenyl.

Examples of SEI forming additives are vinylene carbonate and its derivatives such as vinylene carbonate and methylvinylene carbonate; fluorinated ethylene carbonate and its derivatives such as monofluoroethylene carbonate, cis- and trans-difluorocarbonate; propane sultone and its derivatives; ethylene sulfite and its derivatives; oxalate comprising compounds such as lithium oxalate, oxalato borates including dimethyl oxalate, lithium bis(oxalate) borate, lithium difluoro (oxalato) borate, and ammonium bis(oxalato) borate, and oxalato phosphates including lithium tetrafluoro (oxalato) phosphate; and ionic compounds containing a cation of formula (II)

(II)

wherein
X is CH$_2$ or NR$^a$,
R$^5$ is selected from C$_1$ to C$_6$ alkyl,
R$^6$ is selected from —(CH$_2$)$_u$—SO$_3$—(CH$_2$)$_v$—R$^b$,
—SO$_3$— is —O—S(O)$_2$— or —S(O)$_2$—O—, preferably —SO$_3$— is —O—S(O)$_2$—,
u is an integer from 1 to 8, preferably u is 2, 3 or 4, wherein one or more CH$_2$ groups of the —(CH$_2$)$_u$— alkylene chain which are not directly bound to the N-atom and/or the $SO_3$ group may be replaced by O and wherein two adjacent $CH_2$ groups of the $-(CH_2)_u-$ alkylene chain may be replaced by a C—C double bond, preferably the $-(CH_2)_u-$ alkylene chain is not substituted and u is an integer from 1 to 8, preferably u is 2, 3 or 4, v is an integer from 1 to 4, preferably v is 0, $R^a$ is selected from $C_1$ to $C_6$ alkyl, $R^b$ is selected from $C_1$-$C_{20}$ alkyl, $C_2$-$C_{20}$ alkenyl, $C_2$-$C_{20}$ alkynyl, $C_6$-$C_{12}$ aryl, and $C_6$-$C_{24}$ aralkyl, which may contain one or more F, and wherein one or more $CH_2$ groups of alkyl, alkenyl, alkynyl and aralkyl which are not directly bound to the $SO_3$ group may be replaced by O, preferably $R^b$ is selected from $C_1$-$C_6$ alkyl, $C_2$-$C_4$ alkenyl, and $C_2$-$C_4$ alkynyl, which may contain one or more F, and wherein one or more $CH_2$ groups of alkyl, alkenyl, alkynyl and aralkyl which are not directly bound to the $SO_3$ group may be replaced by O, preferred examples of $R^b$ include methyl, ethyl, trifluoromethyl, pentafluoroethyl, n-propyl, n-butyl, n-hexyl, ethenyl, ethynyl, allyl or prop-1-yn-yl, and an anion selected from bisoxalato borate, difluoro (oxalato) borate, $[F_zB(C_mF_{2m+1})_{4-z}]^-$, $[F_yP(C_mF_{2m+1})_{6-y}]^-$, $(C_mF_{2m+1})_2P(O)O]^-$, $[C_mF_{2m+1}P(O)O_2]^{2-}$, $[O—C(O)—C_mF_{2m+1}]^-$, $[O—S(O)_2—C_mF_{2m+1}]^-$, $[N(C(O)—C_mF_{2m+1})_2]^-$, $[N(S(O)_2—C_mF_{2m+1})_2]^-$, $[N(C(O)—C_mF_{2m+1})(S(O)_2—C_mF_{2m+1})]^-$, $[N(C(O)—C_mF_{2m+1})(C(O)F)]^-$, $[N(S(O)_2—C_mF_{2m+1})(S(O)_2F)]^-$, $[N(S(O)_2F)_2]^-$, $[C(C(O)—C_mF_{2m+1})_3]^-$, $[C(S(O)_2—C_mF_{2m+1})_3]^-$, wherein m is an integer from 1 to 8, z is an integer from 1 to 4, and y is an integer from 1 to 6.

Preferred anions are bisoxalato borate, difluoro (oxalato) borate, $[F_3B(CF_3)]^-$, $[F_3B(C_2F_5)]^-$, $[PF_6]^-$, $[F_3P(C_2F_5)_3]^-$, $[F_3P(C_3F_7)_3]^-$, $[F_3P(C_4F_9)_3]^-$, $[F_4P(C_2F_5)_2]^-$, $[F_4P(C_3F_7)_2]^-$, $[F_4P(C_4F_9)_2]^-$, $[F_5P(C_2F_5)]^-$, $[F_5P(C_3F_7)]^-$, or $[F_5P(C_4F_9)]^-$, $[(C_2F_5)_2P(O)O]^-$, $[(C_3F_7)_2P(O)O]^-$, or $[(C_4F_9)_2P(O)O]^-$, $[C_2F_5P(O)O_2]^{2-}$, $[C_3F_7P(O)O_2]^{2-}$, $[C_4F_9P(O)O_2]^{2-}$, $[O—C(O)CF_3]^-$, $[O—C(O)C_2F_5]^-$, $[O—C(O)C_4F_9]^-$, $[O—S(O)_2CF_3]^-$, $[O—S(O)_2C_2F_5]^-$, $[N(C(O)C_2F_5)_2]^-$, $[N(C(O)(CF_3)_2]^-$, $[N(S(O)_2CF_3)_2]^-$, $[N(S(O)_2C_2F_5)_2]^-$, $[N(S(O)_2C_3F_7)_2]^-$, $[N(S(O)_2CF_3)(S(O)_2C_2F_5)]^-$, $[N(S(O)_2C_4F_9)_2]^-$, $[N(C(O)CF_3)(S(O)_2CF_3)]^-$, $[N(C(O)C_2F_5)(S(O)_2CF_3)]^-$, or $[N(C(O)CF_3)(S(O)_2—C_4F_9)]^-$, $[N(C(O)CF_3)(C(O)F)]^-$, $[N(C(O)C_2F_5)(C(O)F)]^-$, $[N(C(O)C_3F_7)(C(O)F)]^-$, $[N(S(O)_2CF_3)(S(O)_2F)]^-$, $[N(S(O)_2C_2F_5)(S(O)_2F)]^-$, $[N(S(O)_2C_4F_9)(S(O)_2F)]^-$, $[C(C(O)CF_3)_3]^-$, $[C(C(O)C_2F_5)_3]^-$ or $[C(C(O)C_3F_7)_3]^-$, $[C(S(O)_2CF_3)_3]^-$, $[C(S(O)_2C_2F_5)_3]^-$, and $[C(S(O)_2C_4F_9)_3]^-$.

More preferred the anion is selected from bisoxalato borate, difluoro (oxalato) borate, $CF_3SO_3^-$, and $[PF_3(C_2F_5)_3]^-$.

Preferred SEI-forming additives are oxalato borates, fluorinated ethylene carbonate and its derivatives, vinylene carbonate and its derivatives, and compounds of formula (II). More preferred are lithium bis(oxalato) borate (Li-BOB), vinylene carbonate, monofluoro ethylene carbonate, and compounds of formula (II), in particular monofluoro ethylene carbonate, and compounds of formula (II).

A compound added as additive may have more than one effect in the electrolyte composition and the device comprising the electrolyte composition. E.g. lithium oxalato borate may be added as additive enhancing the SEI formation but it may also be added as conducting salt.

In one embodiment of the present disclosure, the electrolyte composition contains:

(i) at least one compound of formula (I), (ii) at least one organic aprotic solvent, (iii) at least one conducting salt, and (iv) optionally at least one further additive.

The further additive is different from the compounds of formula (I).

The electrolyte composition preferably contains (i) in total 0.01 to 10 wt.-% preferred 0.05 to 5 wt.-%, more preferred 0.125 to 2.5 wt.-%, and most preferred 0.25 to 1.5 wt.-%, (ii) in total 60 to 99.89 wt.-% of organic aprotic solvent(s), (iii) in total 0.1 to 25 wt.-% of conducting salt(s), preferably 10 to 20 wt.-%, and (iv) zero to in total 30 wt.-% of further additive(s), preferably 1 to 10 wt.-%, based on the total weight of the electrolyte composition.

The water content of the inventive electrolyte composition is preferably below 100 ppm, based on the weight of the electrolyte composition, more preferred below 50 ppm, most preferred below 30 ppm. The water content may be determined by titration according to Karl Fischer, e.g. described in detail in DIN 51777 or ISO760: 1978.

The content of HF of the inventive electrolyte composition is preferably below 60 ppm, based on the weight of the electrolyte composition, more preferred below 40 ppm, most preferred below 20 ppm. The HF content may be determined by titration according to potentiometric or potentiographic titration method.

The inventive electrolyte composition is preferably liquid at working conditions; more preferred it is liquid at 1 bar and 25° C., even more preferred the electrolyte composition is liquid at 1 bar and −15° C., in particular the electrolyte composition is liquid at 1 bar and −30° C., even more preferred the electrolyte composition is liquid at 1 bar and −50° C.

The electrolyte compositions according to the disclosure are prepared by methods which are known to the person skilled in the field of the production of electrolytes, generally by dissolving the conductive salt in the corresponding solvent mixture and adding the compounds of the formula (I) according to the disclosure and optionally additional additives, as described above.

The electrolyte compositions are used in electrochemical cells like lithium batteries, double layer capacitors, and lithium ion capacitors, preferably the inventive electrolyte compositions are used in lithium batteries and more preferred in lithium ion batteries.

The disclosure further provides an electrochemical cell comprising the electrolyte composition as described above or as described as being preferred. The electrochemical cell may be a lithium battery, a double layer capacitor, or a lithium ion capacitor The general construction of such electrochemical devices is known and is familiar to the person skilled in this art—for batteries, for example, in Linden's Handbook of Batteries (ISBN 978-0-07-162421-3).

Preferably the electrochemical cell is a lithium battery. The term "lithium battery" as used herein means an electrochemical cell, wherein the anode comprises lithium metal or lithium ions sometime during the charge/discharge of the cell. The anode may comprise lithium metal or a lithium metal alloy, a material occluding and releasing lithium ions, or other lithium containing compounds; e.g. the lithium battery may be a lithium ion battery, a lithium/sulphur battery, or a lithium/selenium sulphur battery.

In particular preferred the electrochemical device is a lithium ion battery, i.e. a secondary lithium ion electrochemical cell comprising a cathode comprising a cathode active material that can reversibly occlude and release lithium ions and an anode comprising an anode active material that can reversibly occlude and release lithium ions. The terms "secondary lithium ion electrochemical cell" and "(secondary) lithium ion battery" are used interchangeably within the present disclosure.

The at least one cathode active material preferably comprises a material capable of occluding and releasing lithium ions selected from lithiated transition metal phosphates and lithium ion intercalating metal oxides.

Examples of lithiated transition metal phosphates are LiFePO$_4$ and LiCoPO$_4$, examples of lithium ion intercalating metal oxides are LiCoO$_2$, LiNiO$_2$, mixed transition metal oxides with layer structure having the general formula Li$_{(1+z)}$[Ni$_a$Co$_b$Mn$_c$]$_{(1-z)}$O$_{2+e}$ wherein z is 0 to 0.3; a, b and c may be same or different and are independently 0 to 0.8 wherein a+b+c=1; and −0.1≤e≤0.1, and manganese-containing spinels like LiMnO$_4$ and spinels of general formula Li$_{1+t}$M$_{2-t}$O$_{4-d}$ wherein d is 0 to 0.4, t is 0 to 0.4 and M is Mn and at least one further metal selected from the group consisting of Co and Ni, and Li$_{(1+g)}$[Ni$_h$Co$_i$Al$_j$]$_{(1-g)}$O$_{2+k}$. Typical values for g, h, I, j and k are: g=0, h=0.8 to 0.85, i=0.15 to 0.20, j=0.02 to 0.03 and k=0.

The cathode may further comprise electrically conductive materials like electrically conductive carbon and usual components like binders. Compounds suited as electrically conductive materials and binders are known to the person skilled in the art. For example, the cathode may comprise carbon in a conductive polymorph, for example selected from graphite, carbon black, carbon nanotubes, graphene, or mixtures of at least two of the aforementioned substances. In addition, the cathode may comprise one or more binders, for example one or more organic polymers like polyethylene, polyacrylonitrile, polybutadiene, polypropylene, polystyrene, polyacrylates, polyvinyl alcohol, polyisoprene and copolymers of at least two comonomers selected from ethylene, propylene, styrene, (meth)acrylonitrile and 1,3-butadiene, especially styrene-butadiene copolymers, and halogenated (co)polymers like polyvinlyidene chloride, polyvinly chloride, polyvinyl fluoride, polyvinylidene fluoride (PVdF), polytetrafluoroethylene, copolymers of tetrafluoroethylene and hexafluoropropylene, copolymers of tetrafluoroethylene and vinylidene fluoride and polyacrylnitrile.

The anode comprised within the lithium batteries of the present disclosure comprises an anode active material that can reversibly occlude and release lithium ions or is capable to form an alloy with lithium. In particular carbonaceous material that can reversibly occlude and release lithium ions can be used as anode active material. Carbonaceous materials suited are crystalline carbon such as a graphite material, more particularly, natural graphite, graphitized cokes, graphitized MCMB, and graphitized MPCF; amorphous carbon such as coke, mesocarbon microbeads (MCMB) fired below 1500° C., and mesophase pitch-based carbon fiber (MPCF); hard carbon and carbonic anode active material (thermally decomposed carbon, coke, graphite) such as a carbon composite, combusted organic polymer, and carbon fiber.

Further anode active materials are lithium metal, or materials containing an element capable of forming an alloy with lithium. Non-limiting examples of materials containing an element capable of forming an alloy with lithium include a metal, a semimetal, or an alloy thereof. It should be understood that the term "alloy" as used herein refers to both alloys of two or more metals as well as alloys of one or more metals together with one or more semimetals. If an alloy has metallic properties as a whole, the alloy may contain a nonmetal element. In the texture of the alloy, a solid solution, a eutectic (eutectic mixture), an intermetallic compound or two or more thereof coexist. Examples of such metal or semimetal elements include, without being limited to, titanium (Ti), tin (Sn), lead (Pb), aluminum, indium (In), zinc (Zn), antimony (Sb), bismuth (Bi), gallium (Ga), germanium (Ge), arsenic (As), silver (Ag), hafnium (Hf), zirconium (Zr) yttrium (Y), and silicon (Si). Metal and semimetal elements of Group 4 or 14 in the long-form periodic table of the elements are preferable, and especially preferable are titanium, silicon, and tin, in particular silicon. Examples of tin alloys include ones having, as a second constituent element other than tin, one or more elements selected from the group consisting of silicon, magnesium (Mg), nickel, copper, iron, cobalt, manganese, zinc, indium, silver, titanium (Ti), germanium, bismuth, antimony, and chromium (Cr). Examples of silicon alloys include ones having, as a second constituent element other than silicon, one or more elements selected from the group consisting of tin, magnesium, nickel, copper, iron, cobalt, manganese, zinc, indium, silver, titanium, germanium, bismuth, antimony, and chromium.

A further possible anode active material is silicon based materials. Silicon based materials include silicon itself, silicon containing compounds such as silicon sub-oxide, silicon oxide, and silicon-aluminum alloys and compositions containing silicon and/or silicon containing compounds, e.g. silicon/carbon composites. The silicon may be used in different forms, e.g. in the form of nanowires, nanotubes, nanoparticles, films, nanoporous silicon or silicon nanotubes. The silicon may be deposited on a current collector. The current collector may be a metal wire, a metal grid, a metal web, a metal sheet, a metal foil, or a metal plate. Preferred the current collector is a metal foil, e.g. a copper foil. Thin films of silicon may be deposited on metal foils by any technique known to the person skilled in the art, e.g. by sputtering techniques. One possibility of preparing Si thin film electrodes are described in R. Elazari et al.; Electrochem. Comm. 2012, 14, 21-24.

Other possible anode active materials are lithium ion intercalating oxides of Ti.

Preferably the anode active material is selected from carbonaceous material that can reversibly occlude and release lithium ions, particularly preferred the carbonaceous material that can reversibly occlude and release lithium ions is selected from crystalline carbon, hard carbon, and amorphous carbon, in particular preferred is graphite. In another preferred embodiment the anode active is selected from silicon that can reversibly occlude and release lithium ions, preferably the anode comprises a thin film of silicon or a silicon/carbon composite. In a further preferred embodiment, the anode active is selected from lithium ion intercalating oxides of Ti.

The anode and cathode may be made by preparing an electrode slurry composition by dispersing the electrode active material, a binder, optionally a conductive material and a thickener, if desired, in a solvent and coating the slurry composition onto a current collector. The current collector may be a metal wire, a metal grid, a metal web, a metal sheet, a metal foil, or a metal plate. Preferred the current collector is a metal foil, e.g. a copper foil or aluminum foil.

The inventive lithium batteries may contain further constituents customary per se, for example separators, housings, cable connections etc. The housing may be of any shape, for example cuboidal or in the shape of a cylinder, the shape of a prism or the housing used is a metal-plastic composite film processed as a pouch. Suited separators are for example glass fiber separators and polymer-based separators like polyolefin separators.

Several inventive lithium batteries may be combined with one another, for example in series connection or in parallel connection. Series connection is preferred. The present disclosure further provides for the use of inventive lithium ion batteries as described above in devices, especially in mobile devices. Examples of mobile devices are vehicles, for example automobiles, bicycles, aircraft, or water vehicles such as boats or ships. Other examples of mobile devices are those which are portable, for example computers, especially laptops, telephones, or electrical power tools, for example from the construction sector, especially drills, battery-driven screwdrivers, or battery-driven tackers. But the inventive lithium ion batteries can also be used for stationary energy stores.

Even without further statements, it is assumed that a skilled person is able to utilize the above description in its widest extent. Consequently, the preferred embodiments and examples are to be interpreted merely as a descriptive enclosure which in no way has any limiting effect at all.

The disclosure is illustrated by the examples which follow, which do not, however, restrict the disclosure.

PREPARATION OF COMPOUNDS OF FORMULA (I)

Compound I.1: Methyl-(4-trifluoro-3-(trifluoromethyl))-but-2-enoate

Two reaction vessels, each equipped with a stirrer, were connected to a cold trap. Vessel A was charged with 245 g (2.4 moles) of acetic anhydride and 6 g of concentrated sulfuric acid. Vessel B was charged with 67 g (200 mmol) of methyl(triphenylphosphoranyliden)acetate and 200 ml of pentane and connected to a dry ice reflux condenser. Vessel A was warmed to 50° C., the cold trap was cooled with acetone/dry ice. Into vessel A was introduced 90 g (400 mmol) of hexafluoroacetone trihydrate. The evolving gaseous hexafluoroacetone was condensed in the cold trap. Subsequently, vessel B was cooled with acetone/dry ice and the cold trap was allowed to warm to room temperature. When all of the hexafluoroacetone had evaporated from the cold trap, the temperature in vessel B was raised to −30° C. and the mixture was stirred for three hours. The reaction mixture was allowed to warm to room temperature overnight. The precipitate was filtered off and the pentane was distilled off using a 20 cm distillation column filled with Raschig rings. The liquid residue was distilled at normal pressure on a rotary band column. There was obtained 22.9 g of product with a purity of 98.9% (GC). The product was characterized via its mass spectrum.

Compound I.2: 3-(2,2,2-Trifluoro-1-methyl-ethenyl)-tetrahydrofuran-2-one

In an argon atmosphere, 6.3 g (157 mmol) of sodium hydride (60% in paraffin) were suspended 150 mL of dry tetrahydrofuran (THF). While stirring and cooling with ice water, 33.3 g (150 mmol) 3-(diethylphosphonio)tetrahydrofuran-2-one were added at 0 5° C. After the addition, the temperature was allowed to rise to room temperature and stirring was continued until the evolution of hydrogen had ceased (ca. 1 hour). The reaction mixture was again cooled to 0-5° C. and a solution of 22.4 g (200 mmol) trifluoroacetetone in 50 ml of dry THF was added. The mixture was stirred at 0-5° C. for another hour, then warmed to room temperature. A yellowish jelly formed at the bottom of the flask. The THF was decanted from the jelly and 150 mL of 20% hydrochloric acid were added to the flask. This mixture was extracted with 3×10 ml of diethyl ether. The combined organic phases were washed with water and brine, dried over sodium sulfate and the solvent was evaporated. There was obtained 17.6 grams of colorless liquid.

The previously decanted THF was evaporated under vacuum at 50° C. and a biphasic residue was obtained. The phases were separated and gave 1.7 g of upper phase and 23.5 g of lower phase.

The lower phase was combined with the liquid gained from the acidic work-up of the gelatinous residue and distilled at 0.3-0.4 mbar on a rotary band column. The fraction boiling at 50° C. was collected (8.7 g) and characterized. 1H-NMR (400 MHz): 2.45 ppm (s, 3H), 3.15 ppm (m, 2H), 4.4 ppm (dd, 2H); FT-IR: 1672 cm-1 (C=C), 1788 cm-1, 1808 cm-1 (C=O); FI-HMS: C7H7O2F3.

Compound I.3: Methyl-(4-trifluoro-3-methyl)-but-2-enoate

Under an atmosphere of dry argon, 67.0 g (200 mmol) methyl(triphenylphosphoranylidene)-acetate were suspended in 300 mL of n-pentane and the mixture was cooled to −78° C. 33.6 g of trifluoroacetone were added rapidly and stirring at −78° C. was continued for another three hours. The reaction mixture was allowed to warm to room temperature overnight. The precipitate was filtered by frit and the pentane was distilled off using a 20 cm distillation column filled with Raschig rings. The residue was distilled at normal pressure on a rotary band column. There were obtained 87.3 g of pentane and four fractions boiling from 106-111° C. containing the target product. The first two of these fractions had assays of 67% and 85.6% (GC) and weighed 0.8 and 1.1 g respectively. The last two fractions contained 97.4% and 97.9% of target product (GC) and weighed 8.9 and 11.6 g respectively. The product was characterized via its mass spectrum.

Electrolyte Compositions

Electrolyte compositions were prepared containing 1 M LiPF$_6$ in a mixture of propylene carbonate (PC) or ethylene carbonate (EC) and ethyl methyl carbonate (EMC) in a ratio of 3:7 by mass and 2 or 1 wt.-% of different comparative and inventive compounds as shown in Table 1.

TABLE 1

| Example | Structure | Reduction potential peak vs. Li$^+$/Li [V] |
|---|---|---|
| Compound I.1 (inventive) | [structure of methyl-(4-trifluoro-3-(trifluoromethyl))-but-2-enoate] | 2.07 |

TABLE 1-continued

| Example | Structure | Reduction potential peak vs. Li+/Li [V] |
|---|---|---|
| Compound I.2 (inventive) | 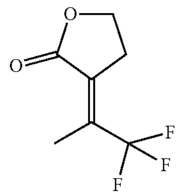 | 1.68 |
| Compound I.3 (inventive) | 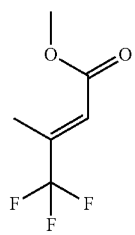 | 1.57 |

TABLE 1-continued

| Example | Structure | Reduction potential peak vs. Li+/Li [V] |
|---|---|---|
| 3.3-dimethylacrylacid methyl ester (comparative) | 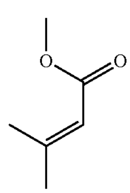 | 0.97 |

Electrochemical Tests

Reduction potential peak values were obtained from differential capacity plots of 2032 coin-type cells comprising a CMC-bonded graphite working electrode on a Cu current collector and a PVDF bonded lithium iron phosphate (LFP, BASF) counter electrode (cell voltages were converted into working electrode potential vs. Li+/Li considering an average counter electrode potential of 3.45 $V_{Li}$). Cells were galvanostatically charged at C/100 rate from open circuit voltage to 3.6 $V_{Li}$ using a composition of EC/EMC 3/7 by weight containing 1M LiPF$_6$ and 2 wt.-% of the respective additive. The results are shown in Table 1.

Capacity retention of Li-ion cells using the inventive electrolyte additives reported below was investigated in a full cell configuration with coin-type cells (2032) with the same anode as described above for the determination of the reduction potential. The cathode used was PVdF (polyvinylidenefluoride)-bonded Li(Ni$_{0.5}$Co$_{0.2}$Mn$_{0.3}$)O$_2$ (also referred to as NCM523, BASF) on an Al current collector. A glass-fiber separator (Whatman GF/D) was used as the separator, which was soaked with 95 μl of a mixture of PC/EMC 3/7 by weight containing 1M LiPF$_6$ and 1 wt.-% of the respective additive. All cells were assembled in an argon-filled glove box (Unilab, MBraun) having oxygen and water levels below 0.1 ppm. Afterwards the test cells were transferred to a battery test station comprising a Maccor battery test system and a climatic chamber tempered at 25° C. Cells were cycled at 0.5 C rate after 2 formation cycles at 0.1 C at 25° C. between 3.0-4.3 V. Capacity retention is reported in Table 2 as percentage of 1$^{st}$ cycle discharge capacity.

The results are shown in Table 2.

TABLE 2

| | 1$^{st}$ cycle capacity | 10$^{th}$ cycle retained 0.5 C capacity (% of 1$^{st}$ cycle) | 20$^{th}$ cycle retained 0.5 C capacity (% of 1$^{st}$ cycle) | 50$^{th}$ cycle retained 0.5 C capacity (% of 1$^{st}$ cycle) |
|---|---|---|---|---|
| Comparative example 1 (3.3-dimethylacrylacid methyl ester) | 0 | 0 | 0 | 0 |
| Inventive example 1 (Compound I.1) | 149.4 | 97.0 | 97.6 | 97.0 |
| Inventive example 2 (Compound I.2) | 160.2 | 98.9 | 98.0 | 95.5 |
| Inventive example 3 (Compound I.3) | 155.1 | 97.2 | 96.0 | 93.2 |

The cell of comparative example 1 with an electrolyte containing a non-fluorinated acrylic acid ester cannot be charged. It is assumed that the failure is caused by exfoliation of the graphite contained in the anode by co-intercalation of propylene carbonate and Li ions present in the electrolyte composition. The acrylic acid ester does not seem to have any effect in respect to the protection of the graphite. The inventive fluorinated acrylic acid esters clearly show good capacity retention and protect the graphitic anode against exfoliation by propylene carbonate.

The invention claimed is:
1. An electrolyte composition comprising:
   at least one additive comprising the compound of formula (I)

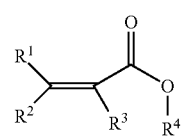

wherein
R¹ and R² are selected from the group consisting of F, CN, R', OR', and OP(O)R"₂,
wherein R' is selected from the group consisting of C1 to C12 alkyl, C3 to C6 (hetero)cycloalkyl, C2 to C12 alkenyl, C2 to C12 alkynyl, C5 to C12 (hetero)aryl, and C6 to C24 (hetero)aralkyl, wherein the alkyl, the (hetero)cycloalkyl, the alkenyl, the alkynyl, the (hetero)aryl, and the (hetero)aralkyl may be substituted by one or more substituents selected from the group consisting of F and CN,
wherein R" is selected from the group consisting of OR' and R' and wherein the two R" may form a 5-membered heterocycle or a 6-membered heterocycle together with the P-atom, and
wherein at least one of R¹ and R² is F or is selected from the group consisting of R', OR', and OP(O)R"₂, in which R' or R" is substituted by one or more F;
R³ is selected from the group consisting of H, C1 to C12 alkyl, C3 to C6 (hetero)cycloalkyl, C2 to C12 alkenyl, C2 to C12 alkynyl, C5 to C12 (hetero)aryl, and C6 to C24 (hetero)aralkyl, wherein the alkyl, the (hetero)cycloalkyl, the alkenyl, the alkynyl, the (hetero)aryl, and the (hetero)aralkyl may be substituted by one or more substituents selected from the group consisting of F and CN;
R⁴ is selected from the group consisting of C1 to C12 alkyl, C3 to C6 (hetero)cycloalkyl, C2 to C12 alkenyl, C2 to C12 alkynyl, C5 to C12 (hetero)aryl, and C6 to C24 (hetero)aralkyl, wherein the alkyl, the (hetero)cycloalkyl, the alkenyl, the alkynyl, the (hetero)aryl, and the (hetero)aralkyl may be substituted by one or more substituents selected from the group consisting of F and CN;
or
R³ and R⁴ are bound together with the group —C—C(O)—O— and form a 5-membered heterocycle or a 6-membered heterocycle which may be substituted by one or more substituents selected from the group consisting of F and C1 to C12 alkyl, wherein the C1 to C12 alkyl may be substituted with one or more F;
wherein the electrolyte composition contains in total 0.1 to 10 wt. % of the at least one additive compound of formula (I), based on the total weight of the electrolyte composition;
(ii) at least one aprotic organic solvent; and
(iii) at least one lithium conducting salt.

2. The electrolyte composition according to claim 1, wherein at least one of R¹ and R² is selected from the group consisting of F and C1 to C12 alkyl, wherein the C1 to C12 alkyl may be substituted with one or more F.

3. The electrolyte composition according to claim 1, wherein both R¹ and R² are selected from the group consisting of F and C1 to C12 alkyl, wherein the C1 to C12 alkyl may be substituted with one or more F.

4. The electrolyte composition according to claim 1, wherein at least one of R¹ and R² is a perfluorinated C1 to C12 alkyl.

5. The electrolyte composition according to claim 1, wherein R³ is selected from the group consisting of H and C1 to C12 alkyl.

6. The electrolyte composition according to claim 1, wherein R⁴ is selected from the group consisting of H and C1 to C12 alkyl, wherein C1 to C12 alkyl may be substituted by one or more substituents selected from F and CN.

7. The electrolyte composition according to claim 1, wherein the at least one compound of formula (I) is selected from the compounds of formulae (1.1) to (1.4)

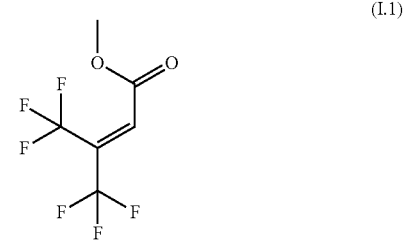
(I.1)

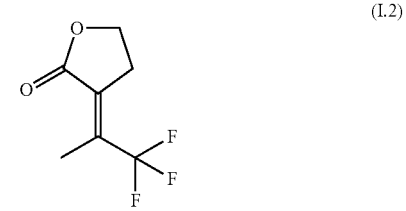
(I.2)

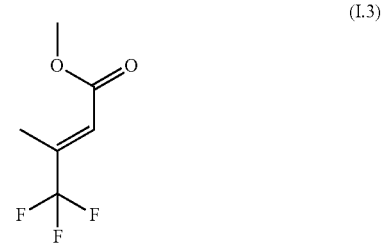
(I.3)

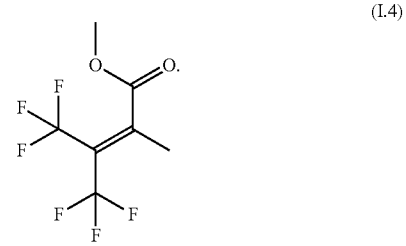
(I.4)

8. An electrochemical cell comprising the electrolyte composition according to claim 1.

9. The electrochemical cell according to claim 8 wherein the electrochemical cell is a lithium battery.

10. The electrolyte composition according to claim 1, wherein the electrolyte composition further comprises at least one further additive different from the compounds of formula (I), wherein the at least one further additive is selected from the group consisting of polymers, SEI forming additives, flame retardants, overcharge protection additives, wetting agents, HF and/or H₂O scavengers, stabilizer for LiPF₆ salt, ionic salvation enhancer, corrosion inhibitors, and gelling agents.

* * * * *